(12) United States Patent
Maurice et al.

(10) Patent No.: US 9,482,748 B2
(45) Date of Patent: Nov. 1, 2016

(54) ULTRASOUND IMAGING SYSTEM, AND A PROCESSING DEVICE USED INSIDE SAID ULTRASOUND IMAGING SYSTEM

(75) Inventors: Francois Maurice, Draguignan (FR); Nicolas Felix, Aix-en-Provence (FR)

(73) Assignee: SUPER SONIC IMAGINE, rue René Descartes (FR)

( * ) Notice: Subject to any disclaimer, the term of this patent is extended or adjusted under 35 U.S.C. 154(b) by 178 days.

(21) Appl. No.: 14/363,768

(22) PCT Filed: Dec. 12, 2011

(86) PCT No.: PCT/IB2011/003328
§ 371 (c)(1),
(2), (4) Date: Jun. 6, 2014

(87) PCT Pub. No.: WO2013/088196
PCT Pub. Date: Jun. 20, 2013

(65) Prior Publication Data
US 2014/0347954 A1    Nov. 27, 2014

(51) Int. Cl.
*G01S 7/52* (2006.01)
*A61B 8/00* (2006.01)
*G01S 7/03* (2006.01)

(52) U.S. Cl.
CPC .......... *G01S 7/52017* (2013.01); *A61B 8/4411* (2013.01); *G01S 7/5208* (2013.01); *G01S 7/52082* (2013.01); *G01S 7/034* (2013.01)

(58) Field of Classification Search
CPC ............. A61B 8/4411; G01S 7/52082; G01S 7/5208; G01S 7/52017; G01S 7/034
See application file for complete search history.

(56) References Cited

U.S. PATENT DOCUMENTS

| | | | |
|---|---|---|---|
| 5,569,853 A | 10/1996 | Mignot | |
| 5,787,889 A | 8/1998 | Edwards et al. | |
| 5,795,297 A | 8/1998 | Daigle | |
| 6,629,928 B1 | 10/2003 | Dolan et al. | |
| 2007/0239001 A1* | 10/2007 | Mehi | G01S 7/52017 600/437 |
| 2009/0054770 A1 | 2/2009 | Daigle | |
| 2011/0074792 A1 | 3/2011 | Li | |
| 2014/0347954 A1* | 11/2014 | Maurice | A61B 8/4411 367/7 |

FOREIGN PATENT DOCUMENTS

| | | |
|---|---|---|
| JP | 61-099864 | 5/1986 |
| JP | 2-182247 | 7/1990 |
| JP | 4-354944 | 12/1992 |
| JP | 8-280679 | 10/1996 |
| JP | 2009-514600 A | 4/2009 |
| WO | WO-2007/056104 A2 | 5/2007 |

OTHER PUBLICATIONS

Search Report for PCT/IB2011/003328, mailed Sep. 10, 2012.
Written Opinion for PCT/IB2011/003328, mailed Sep. 10, 2012.

* cited by examiner

*Primary Examiner* — Daniel Pihulic
(74) *Attorney, Agent, or Firm* — Marshall, Gerstein & Borun LLP

(57) ABSTRACT

The ultrasound imaging system comprises an ultrasound probe (3) and computer (20) for controlling the ultrasound probe and for visualizing an image. The system comprises a processing device located between the probe and the computer that comprises a processing unit (15) to operate an imaging method and switch unit (13) for routing the input and output data.

16 Claims, 7 Drawing Sheets

ULTRASOUND IMAGING SYSTEM, AND A PROCESSING DEVICE USED INSIDE SAID ULTRASOUND IMAGING SYSTEM

FIELD OF THE INVENTION

The present invention concerns an ultrasound imaging system.

BACKGROUND OF THE INVENTION

It is known an ultrasound imaging system comprising:
an ultrasound probe comprising a plurality of transducers for emitting and receiving an ultrasound wave inside a medium, a received ultrasound wave being sensed by said transducers and being converted into input data by at least one analog to digital converter, and
a computer receiving said input data through a data channel and processing these input data to provide an image representing a portion of said medium.

According to a first known embodiment, illustrated on the FIG. 1, a digital acquisition board (DAB), that is an interface board, is located between the ultrasound probe and the computer. Such interface board comprises a programmable logic device (PLD), usually a FPGA circuit, or a digital signal processor (DSP) for processing a beamforming process on at least a predetermined and limited number of signals. The beamformed data are then transmitted to the computer via a data channel.

In that case, the interface board comprises a predetermined and limited number of input signals, and the PLD or DSP has a limited computational power. If the number of transducers is increased, a new interface board must be designed, which is very expensive.

According to a second known embodiment, illustrated in the FIG. 2, the digital acquisition board (DAB) or interface board is located between the ultrasound probe and the computer. The interface board sends all the sensed signal samples (input data) to the computer by multiplexing them into a data channel.

Depending on the number of transducers, the data channels existing inside a standard computer are usually not able to absorb the input data rate from the transducers. Even though the data channels are efficient, the microprocessor of the computer is then unable to operate the beamforming process upon such a huge quantity of input data.

OBJECTS AND SUMMARY OF THE INVENTION

One object of the present invention is to provide an ultrasound imaging system so that the above limitations are removed.

To this effect, the ultrasound imaging system comprises a processing device located between the probe and the computer, and said processing device comprises:
a first channel for receiving the input data corresponding to the received ultrasound wave,
a second channel for transmitting output data to the computer,
at least a processing unit comprising a memory or connected to a memory, said memory being adapted to store the input data and the output data, and said processing unit being adapted to operate an imaging method based upon said input data and to provide the output data, and
a switch unit for routing the input data directly from the first channel to said memory and for routing the output data from said memory to the second channel.

Thanks to these features, the ultrasound imaging device is able to manage a first channel high rate from the probe to the memory, and is able to manage a second channel low rate from the memory to the computer. Such ultrasound imaging device architecture is therefore not dependent to the number of transducers, and it is easily scalable.

The processing unit can be chosen in a list of processing unit having a channel compatible with said switch unit. The processing unit can be a standard commercial processing unit, and is not expensive.

The computer does not need to be a powerful computer. A laptop computer may be used. The ultrasound imaging system is therefore more compact and less expensive.

In various embodiments of the ultrasound imaging device, one and/or other of the following features may optionally be incorporated.

According to another aspect of the invention:
the second channel is a bidirectional channel, and is further adapted for receiving a processing program and processing data from the computer,
the memory is further adapted for storing the processing program and the processing data, and
the switch is further adapted for routing the processing program and the processing data from the computer to the memory through said second channel.

According to another aspect of the invention, the second channel is a PCI express bus.

According to another aspect of the invention, the processing unit and the memory form a sub-assembly that is connected to the switch unit via a PCI express bus.

According to another aspect of the invention, the switch unit is a PCI express switch.

According to another aspect of the invention, the processing unit and the memory form a sub-assembly that is integrated inside a single electronic board.

According to another aspect of the invention, the processing unit and the memory are integrated inside a single electronic circuit.

According to another aspect of the invention, the processing unit is a graphic processing unit.

According to another aspect of the invention, the ultrasound imaging system comprises:
a plurality of processing devices, and
a system switch for routing the output data from each second channel of each processing devices to a third channel connected to the computer.

According to another aspect of the invention, the input and second channels of each processing units are PCI express buses and the third channel is a PCI express bus.

Another object of the invention is to provide a processing device for use in an ultrasound imaging system, said ultrasound imaging system comprising:
at least an ultrasound probe comprising a plurality of transducers for emitting and receiving an ultrasound wave inside a medium, a received ultrasound wave being sensed by said transducers and converted into input data by at least one analog to digital converter, and
a computer adapted at least for controlling the ultrasound probe and for visualizing an image representing a portion of said medium,
wherein the processing device is located between the ultrasound probe and the computer, and comprises:

a first channel for receiving the input data corresponding to the received ultrasound wave, a second channel for transmitting the output data to the computer, at least a processing unit comprising a memory or connected to a memory, said memory being adapted to store the input data and the output data, and said processing unit being adapted to operate an imaging method based upon said input data and to provide the output data, and a switch unit for routing the input data directly from the first channel to said memory and for routing the output data from said memory to the second channel.

In preferred embodiments of the processing device, one and/or the other of the following features may optionally be incorporated.

According to another aspect of the invention:

the second channel is a bidirectional channel, and is further adapted for receiving a processing program and processing data from the computer, the memory is further adapted for storing the processing program and the processing data, and the switch is further adapted for routing the processing program and the processing data from the computer to the memory through said second channel.

According to another aspect of the invention, the first channel is a PCI express bus.

According to another aspect of the invention, the second channel is a PCI express bus.

According to another aspect of the invention, the switch unit is a PCI express switch.

According to another aspect of the invention, the processing unit is a graphic processing unit.

BRIEF DESCRIPTION OF THE DRAWINGS

Other features and advantages of the invention will be apparent from the following detailed description of four of its embodiments given by way of non-limiting example, with reference to the accompanying drawings. In the drawings.

MORE DETAILED DESCRIPTION

In the various figures, the same reference numbers indicate identical or similar elements.

Figure 1:
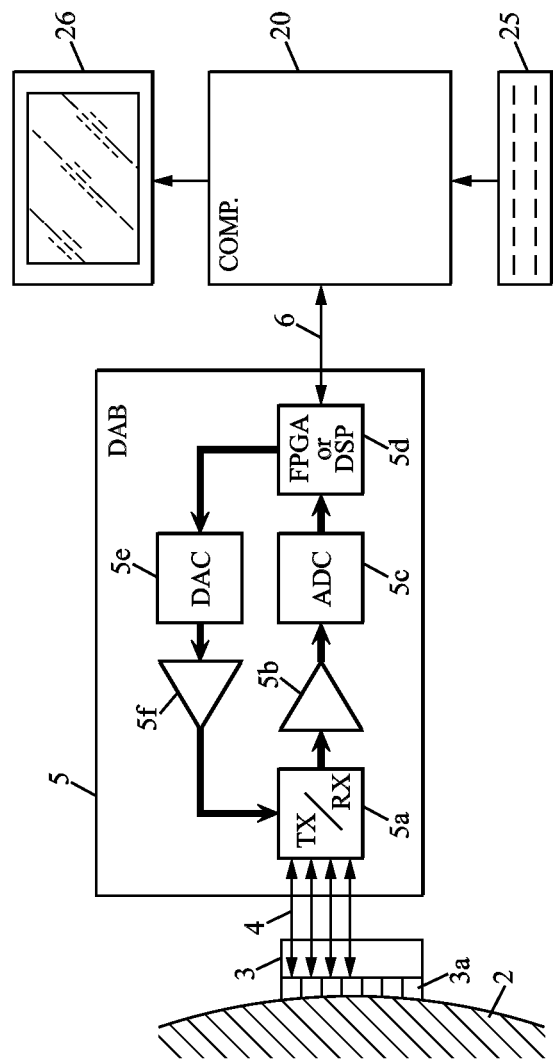
FIG. 1 is an ultrasound imaging system according to a first prior art embodiment wherein the beamforming process is carried out by an interface board.

Referring back to the prior art FIG. 1, such known ultrasound imaging system comprises:

a probe 3 having a plurality of transducers 3a, for emitting and receiving an ultrasound wave inside a medium 2, and providing transducers signals 4, a digital analog board (DAB) 5 connected to said probe 3, receiving the transducers signals and providing data on a second channel 6, and a computer 20 receiving said data from the DAB 5.

The DAB 5 comprises an analog transmitter receiver multiplexer 5a connected to said transducers 3a, a plurality of amplifiers 5b to amplify the transducers signals into amplified signals, and analog to digital converters (ADC) 5c to convert the amplified signals into first digital values and providing said first digital values to a circuit 5d, said circuit 5d being a programmable logic device (PLD) 7b, for example a field-programmable gate array (FPGA) or a digital signal processor (DSP).

The circuit 5d implements a logic corresponding to a beamforming method and provides output data of beamformed data on the second channel 6 for the computer 20.

The implemented beamformed method is programmed inside the circuit 5d during the system start up from the computer 20 or from an on-board flash memory, and can hardly be changed after. The implemented beamformed method can process a predetermined number of transducers signals. Therefore, such ultrasound imaging system architecture is predetermined at manufacturing; it is not modular and not easily scalable. For example, any change in the number of transducers signals or any change in the imaging method, will incur the need to design a new board or at least to program a new circuit 5d. Additionally, the known circuits are not enough powerful if the number of transducers signals increases a lot, and for example for a number of transducers signals higher than two hundreds, the known circuits 5d are not able to process a beamforming method on these signals.

As usual, the computer 20 comprises:

a keyboard 25 for inputting information or control command from a user, and a screen 26 for visualising beamformed image to said user.

The second channel 6 is a bidirectional channel. The computer 20 also provides second digital values to the DAB 5 for emitting an ultrasound wave inside the medium 2.

The circuit 5d sends said second digital values to a digital analog converter 5e to produce signals. These signals are amplified by an amplifier 5f, and multiplexed by the analog transmitter receiver multiplexer 5a. The amplified signals are therefore sent to the probe transducers 3a for generating an ultrasound wave inside the medium 2.

Figure 2:
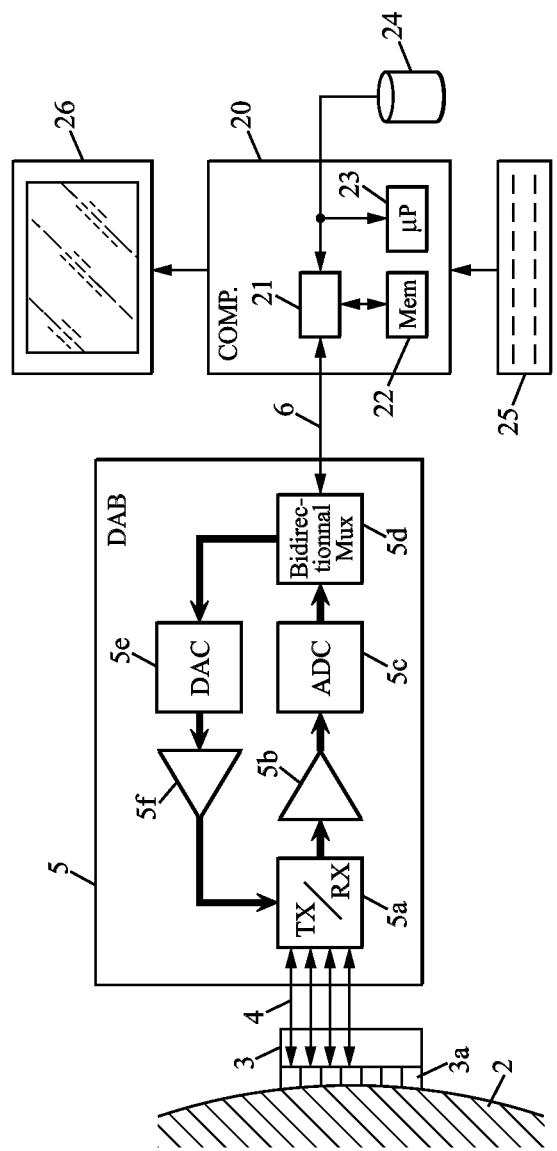
FIG. 2 is an ultrasound imaging system according to a second prior art embodiment wherein beamforming process is carried out by the computer.

Referring to the prior art FIG. 2, such known ultrasound imaging system differs from the first one by its circuit 5d. The circuit 5d is here only a bidirectional multiplexer that provides the first digital values from the ADC 5c to the computer 20 via the second channel 6, and that provides the second digital values from the computer 20 via the second channel 6 to the DAC 5e.

The computer 20 comprises a bridge 21 that interconnects the computer inner data channels. The bridge 21 connects the second channel 6 from the DAB 5, a memory 22 and a microprocessor 23. The computer 20 executes a beamforming software stored inside an hard drive 24. The beamforming software implements a beamforming method that uses the first digital values from the transducers. For example, the beamforming software implements known beamforming method, wherein the first digital values from the plurality of transducers 3a are each delayed with a predetermined delay, and summed together to compute an image of a slice inside the medium 2.

Such ultrasound imaging system is modular and scalable. However, all the first digital values are transferred to the computer 20 and all the data processing is done by the computer 20. If the number of transducers is huge, for example several hundreds, the data channels usually embedded inside a standard computer, such as a USB or PCI express, are not able to absorb directly the input data rate from these transducers. A plurality of data channels may be used in parallel to increase the allowable rate, but the microprocessor and optional coprocessor embedded inside the computer may then be unable to operate the beamforming process upon such huge quantity of input data.

Therefore, even if such ultrasound imaging system architecture is pleasant and completely modular, it can not be carried out for a huge number of transducers, and therefore can not be carried out for producing accurate 2D real time images or for 3D images.

Figure 3:
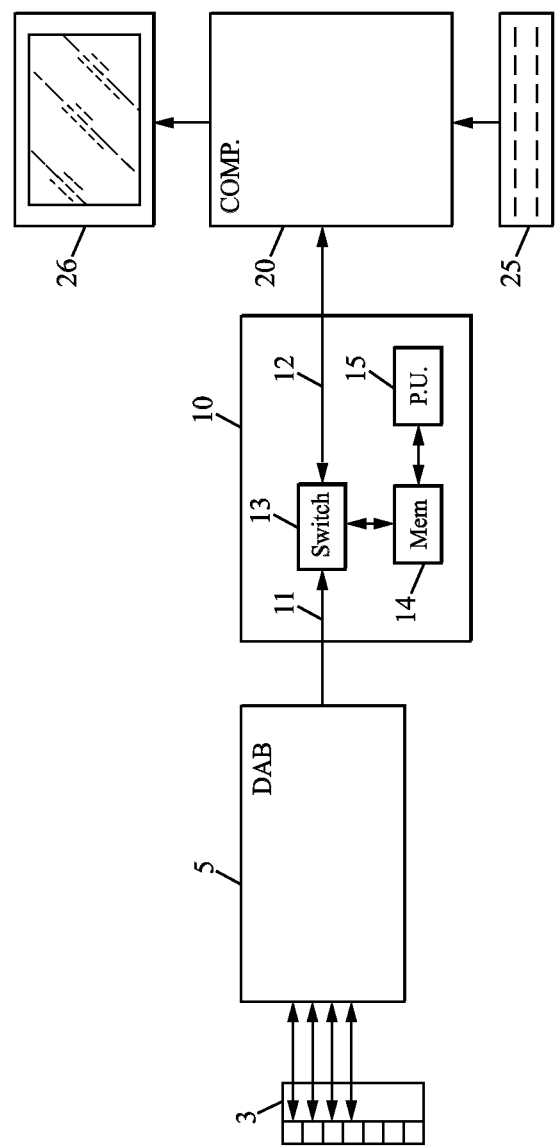
FIG. 3 is an ultrasound imaging system according to a first embodiment of the invention.

FIG. 3 represents an ultrasound imaging system according to present invention that comprises a processing device 10 located between the probe 3 and the computer 20.

In this first embodiment, the system comprises a DAB 5 after the probe 3. The processing device 10 is therefore connected between the DAB 5 and the computer 20.

The processing device 10 comprises at least:
a first channel 11 for receiving the input data corresponding to the received ultrasound wave,
a second channel 12 for transmitting output data to the computer,
at least a processing unit 15 comprising a memory 14 or connected to a memory 14, and
a switch unit 13 for routing the input data directly from the first channel to said memory and for routing the output data from said memory to the second channel.

The memory 14 is adapted to store the input and output data.

The processing unit 15 is adapted to process a beamforming method or any imaging method based upon said input data, so that to provide the output data.

The processing unit 15 may be a graphic processing unit (GPU).

The switch unit 13 is therefore able to manage different channel rates. The second channel rate can be low, and the computer can be a low cost computer. Thanks to such architecture comprising a switch unit, the ultrasound imaging system is scalable.

The first channel may be a PCI express bus, or a USB bus, or the like.

The second channel may be a PCI express bus, or a USB bus, or the like.

The memory 14 and the processing unit 15 may form a sub-assembly. Such sub-assembly may be integrated inside a single electronic board.

The sub-assembly may be connected to the switch unit 13 via a PCI express bus or the like.

The sub-assembly may be a Mobile PCI-Express Module (MXM).

Thanks to these features, the processing device 10 may use standard commercial processing units that are low cost. The ultrasound imaging system of the invention is less expensive than the equivalent (having same number of transducers) and than the prior art systems.

The second channel 12 is advantageously a bidirectional channel. The computer 20 can therefore provide digital values to the DAC 5e for generating the emitted ultrasound wave inside the medium 2.

Advantageously, the second channel 12 is also adapted for providing at least a processing program and processing data from the computer 20 to the memory 14, said processing program being the program that implements a beamforming or an imaging method. The processing unit 15 is then able to operate this processing program stored in memory 14.

The processing program can be updated or changed, and the ultrasound imaging system is scalable and upgradable.

Thanks to the switch 13 and the second channel 12, the processing unit 15 is seen from the computer as an internal resource; as it is located inside the computer 20. In case of a plurality of processing units 15, they are all seen as inside the computer. The program implementing the imaging method is easily developed because the program developed for the second prior art is very similar, and need only minor changes to be adapted to the new ultrasound imaging system architecture.

Figure 4:
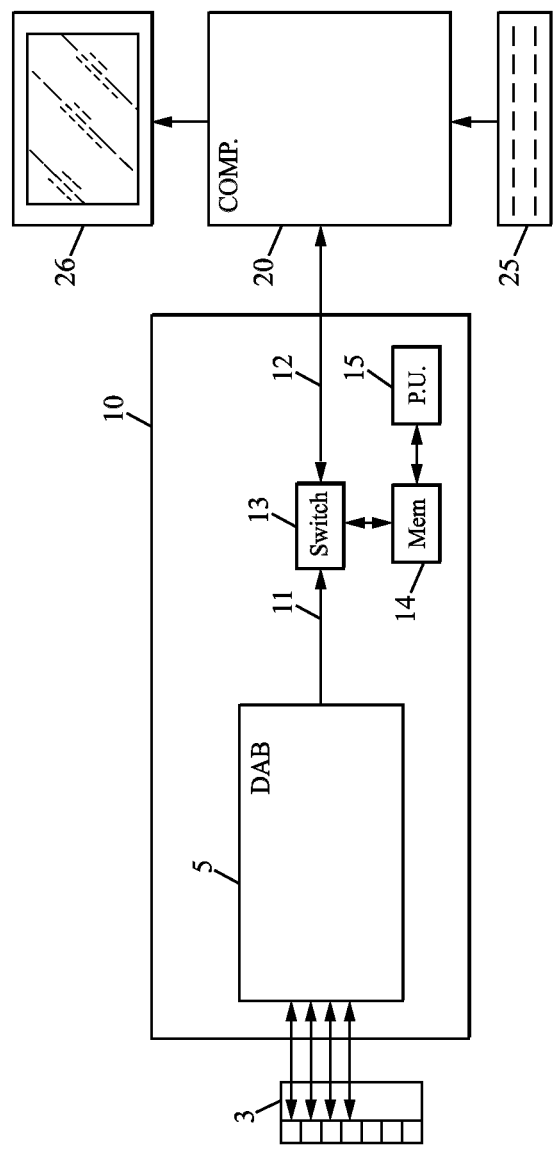
FIG. 4 is an ultrasound imaging system according to a second embodiment of the invention.

FIG. 4 represents a second embodiment of the invention, wherein the DAB 5 located after the probe 3 is integrated inside the processing device 10 before the switch unit 13. The first channel 11 is inside the processing device 10 and connects the DAB 5 to the switch unit 13.

Figure 5:
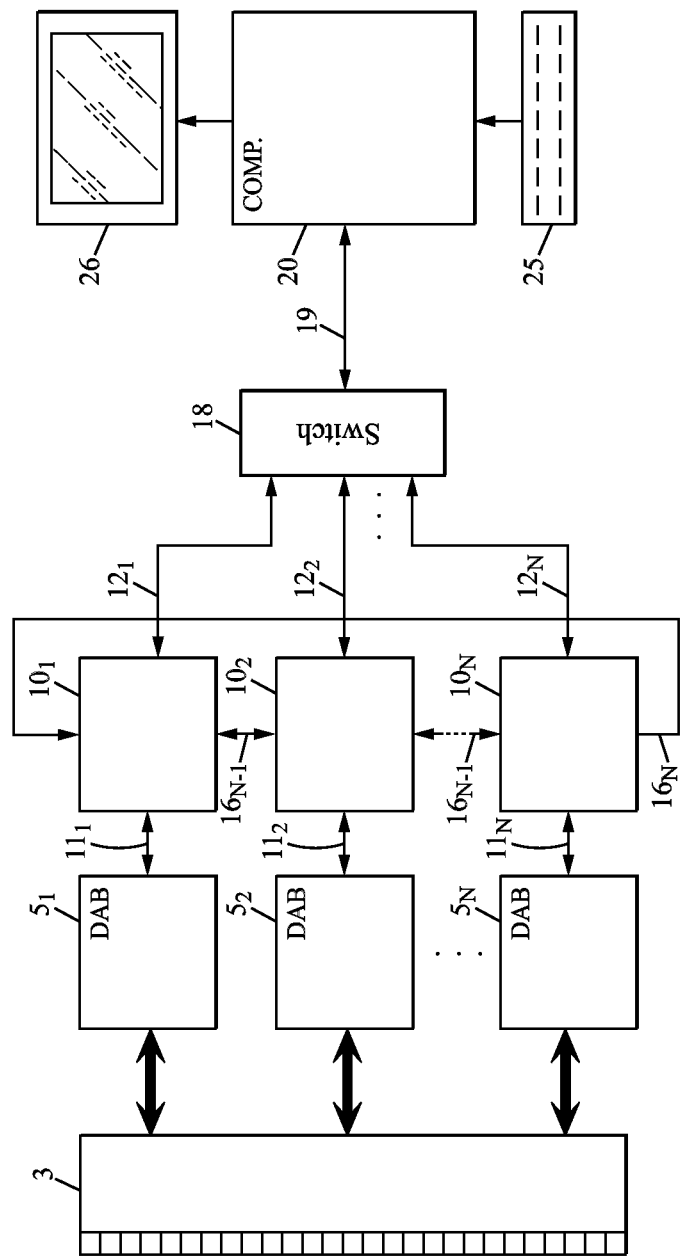
FIG. 5 is an ultrasound imaging system according to a third embodiment of the invention.

FIG. 5 represents a third embodiment of the invention comprising a plurality of processing devices $10_1 \ldots 10_N$. The system comprises a number N of processing devices. Each processing device $10_i$, i representing an index value between 1 and N, is connected:
at its input to a corresponding DAB $5_i$ via a corresponding first channel $11_i$, and
at its output to a system switch 18 via a second channel $12_i$.

The system switch 18 gathers all the output data from all the processing devices $10_1 \ldots 10_N$ and sends these data to the computer 20 via a third channel 19 (system channel).

Thanks to such architecture, the ultrasound imaging system is scalable. The computing power of all the processing devices grows with the number of transducers. The computer 20 is independent to said transducers number, and can still be a laptop computer.

The processing devices $10_i$ may also be connected to each other via an optional connexion channel $16_i$, in a linear architecture as represented on FIG. 5: A processing device i is connected to the next one via the connexion channel $16_i$. The last processing device $10_N$ is connected to the first processing device $10_1$ via the last connexion channel $16_N$.

In this embodiment, the switch unit 13 of each processing device $10_i$ comprises a first additional channel for connecting the previous processing device and a second additional channel for connecting the next processing device $10_{i+1}$.

Thanks to these features the processing units $15_1 \ldots 15_N$ of the system may communicate to each other, to operate a more complex imaging method based on a number of transducers higher than the number of transducers connected to one DAB 5.

Figure 6:
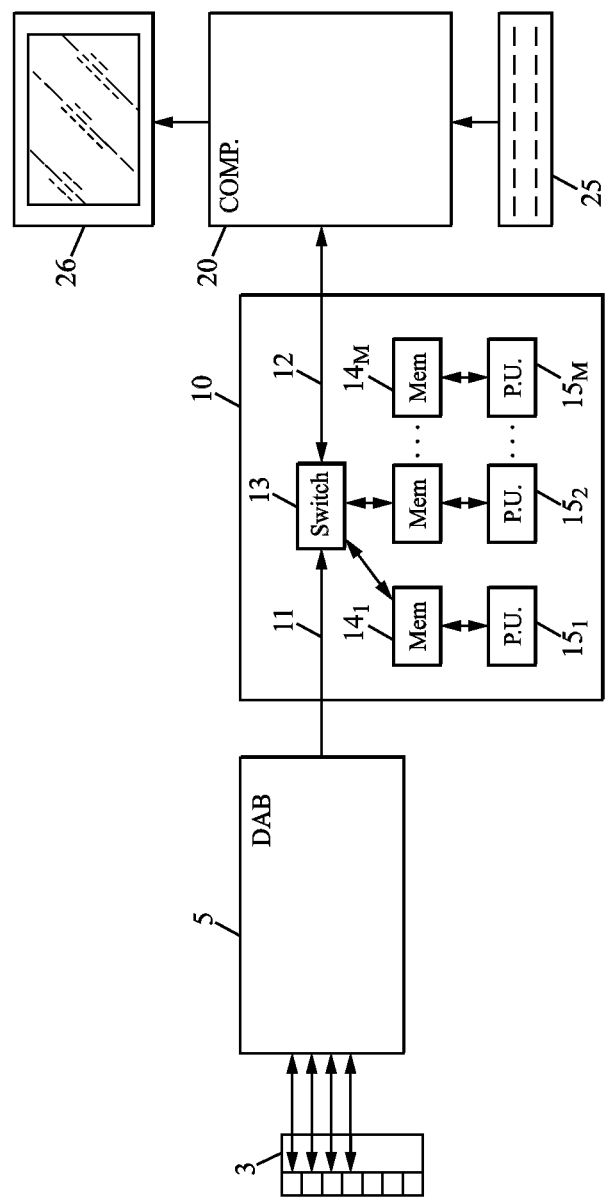
FIG. 6 is an ultrasound imaging system according to a fourth embodiment of the invention.

FIG. 6 represents a fourth embodiment of an ultrasound imaging system wherein the processing device 10 comprises a plurality of sub-assemblies, each of one comprising a memory $14_j$ and a processing unit $15_j$, j being an index comprised between 1 and M, M being a number of sub-assemblies. Each assembly is connected to the switch unit 13 via a connexion channel.

The connexion channel may be a PCI Express bus or the like.

Figure 7:
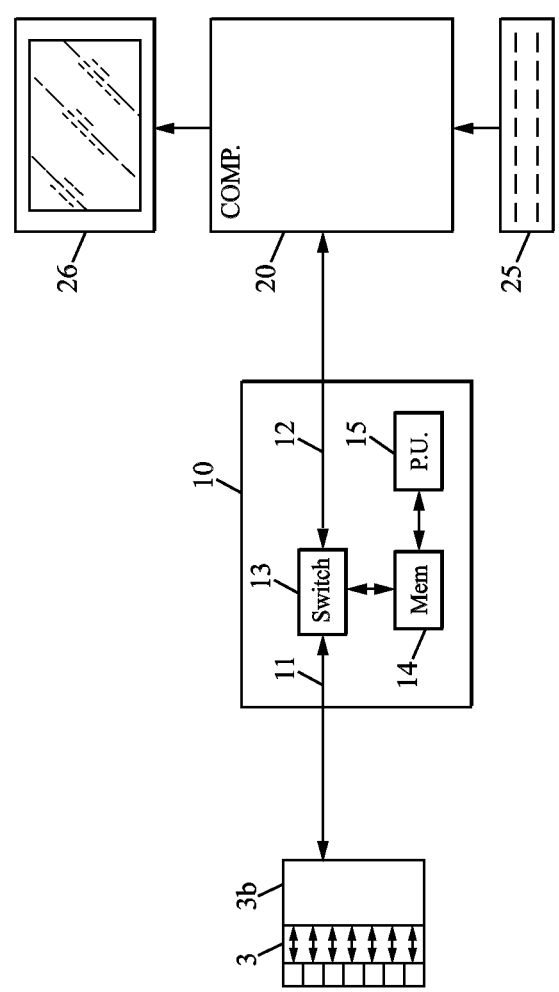
FIG. 7 is an ultrasound imaging system according to a fifth embodiment of the invention.

FIG. 7 represents a fifth embodiment of an ultrasound imaging system, wherein the probe 3 comprises the DAC and ADC 3b. The probe is therefore a digital probe outputting directly digital values. The probe 3 is then directly connected to the switch unit 13 of the processing device 10 via the first channel 11.

In this embodiment, the first channel 11 may be a USB 3.0 bus.

The features of this fifth embodiment may be used in all previous embodiments to provide a full digital architecture to the ultrasound imaging device.

The second channels in the previous embodiments are advantageously PCI express buses. Each of them may comprise a plurality of lane (between 1 and 32 lanes). The number of used lanes can be adapted to the needed rate for a predetermined ultrasound imaging system, and depending on the number of transducers, the imaging method used. Thanks to this feature the ultrasound imaging system is again more scalable.

Such new architecture of ultrasound imaging system makes it now possible to build a fast 3D ultrasound imaging system.

The invention claimed is:

1. An ultrasound imaging system comprising:
   at least an ultrasound probe comprising a plurality of transducers for emitting and receiving an ultrasound wave inside a medium, a received ultrasound wave being sensed by said transducers and converted into input data by at least one analog to digital converter, and
   a computer adapted at least for controlling the ultrasound probe and for visualizing an image representing a portion of said medium,
   wherein the ultrasound imaging system comprises a processing device located between the probe and the computer, and said processing device comprises:
   a first channel for receiving the input data corresponding to the received ultrasound wave,
   a second channel for transmitting output data to the computer,
   at least a processing unit comprising a memory or connected to a memory, said memory being adapted to store the input data and the output data, and said processing unit being adapted to operate an imaging method based upon said input data and to provide the output data, and
   a switch unit connected to the first channel, to second channel and to the processing unit, said switch unit being adapted for routing the input data directly from the first channel to said memory and for routing the output data from said memory to the second channel.

2. The ultrasound imaging system according to claim 1, wherein
   the second channel is a bidirectional channel, and is further adapted for receiving a processing program and processing data from the computer,
   the memory is further adapted for storing the processing program and the processing data, and
   the switch is further adapted for routing the processing program and the processing data from the computer to the memory through said second channel.

3. The ultrasound imaging system according to claim 1, wherein the second channel is a PCI express bus.

4. The ultrasound imaging system according to claim 1, wherein the processing unit and the memory form a subassembly that is connected to the switch unit via a PCI express bus.

5. The ultrasound imaging system according to claim 1, wherein the switch unit is a PCI express switch.

6. The ultrasound imaging system according to claim 1, wherein the processing unit and the memory form a subassembly that is integrated inside a single electronic board.

7. The ultrasound imaging system according to claim 1, wherein the processing unit and the memory are integrated inside a single electronic circuit.

8. The ultrasound imaging system according to claim 1, wherein the processing unit is a graphic processing unit.

9. The ultrasound imaging system according to claim 1, comprising:
   a plurality of processing devices and
   a system switch for routing the output data from each second channel of each processing devices to a third channel connected to the computer.

10. The ultrasound imaging system according to claim 9, wherein the input and second channels of each processing units are PCI express buses and the third channel is a PCI express bus.

11. A processing device for use in an ultrasound imaging system, said ultrasound imaging system comprising:
    at least an ultrasound probe comprising a plurality of transducers for emitting and receiving an ultrasound wave inside a medium, a received ultrasound wave being sensed by said transducers and converted into input data by at least one analog to digital converter, and
    a computer adapted at least for controlling the ultrasound probe and for visualizing an image representing a portion of said medium,
    wherein the processing device is located between the ultrasound probe and the computer, and comprises:
    a first channel for receiving the input data corresponding to the received ultrasound wave,
    a second channel for transmitting the output data to the computer,
    at least a processing unit comprising a memory or connected to a memory, said memory being adapted to store the input data and the output data, and said processing unit being adapted to operate an imaging method based upon said input data and to provide the output data, and
    a switch unit connected to the first channel, to second channel and to the processing unit, said switch unit being adapted for routing the input data directly from the first channel to said memory and for routing the output data from said memory to the second channel.

12. The processing device according to claim 11:
    the second channel is a bidirectional channel, and is further adapted for receiving a processing program and processing data from the computer,
    the memory is further adapted for storing the processing program and the processing data, and
    the switch is further adapted for routing the processing program and the processing data from the computer to the memory through said second channel.

13. The processing device according to claim 11, wherein the first channel is a PCI express bus.

14. The processing device according to claim 11, wherein the second channel is a PCI express bus.

15. The processing device according to claim 11, wherein the switch unit is a PCI express switch.

16. The processing device according to claim 11, wherein the processing unit is a graphic processing unit.

* * * * *